(12) United States Patent
Noack et al.

(10) Patent No.: US 6,376,267 B1
(45) Date of Patent: Apr. 23, 2002

(54) SCATTERED INCIDENT X-RAY PHOTONS FOR MEASURING SURFACE ROUGHNESS OF A SEMICONDUCTOR TOPOGRAPHY

(75) Inventors: Brooke M. Noack, Round Rock; Tim Z. Hossain, Austin, both of TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/265,180

(22) Filed: Mar. 10, 1999

(51) Int. Cl.[7] ............................................. H01L 21/66
(52) U.S. Cl. ........................ 438/16; 438/7; 438/964; 378/70; 378/86
(58) Field of Search ...................... 438/7, 16, 964, 438/14; 356/237.4; 378/70, 74, 86, 87, 88, 89, 90

(56) References Cited

U.S. PATENT DOCUMENTS

| | | | |
|---|---|---|---|
| 5,625,613 A | * 4/1997 | Kato et al. | 369/112 |
| 5,742,658 A | * 4/1998 | Tiffin et al. | 378/44 |
| 5,778,039 A | * 7/1998 | Hossain et al. | 378/45 |
| 6,005,915 A | * 12/1999 | Hossain et al. | 378/86 |
| 6,067,154 A | * 5/2000 | Hossain et al. | 356/237.2 |
| 6,291,363 B1 | * 9/2001 | Yin et al. | 438/769 |

* cited by examiner

Primary Examiner—Kevin M. Picardat
(74) Attorney, Agent, or Firm—Kevin L. Daffer; Conley, Rose & Tayon P.C.

(57) ABSTRACT

A method is presented which uses glancing-angle X-ray fluorescence techniques to determine the roughness of a target surface. A primary X-ray beam is incident upon the target surface at an angle of incidence of less than about 0.2 degrees. Intensities of the elastically scattered primary radiation peak and at least one emitted secondary radiation peak are recorded. The experimental conditions are varied, preferably by changing the angle of incidence of the primary beam slightly, to generate a set of scattered primary and emitted secondary peak intensities. The secondary peak intensity may then be plotted against the scattered primary peak intensity. The plotted points form a line, and the slope of the line is determined. This slope depends on the roughness of the sample surface. The exact roughness may be obtained by comparing the slope to calibration data obtained using direct roughness measurements by a technique such as atomic force microscopy.

19 Claims, 5 Drawing Sheets

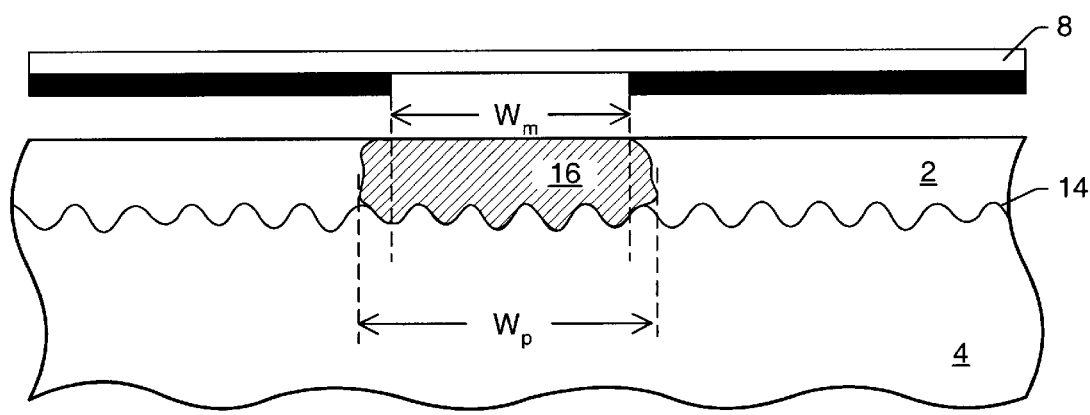
*Fig. 3*
(PRIOR ART)
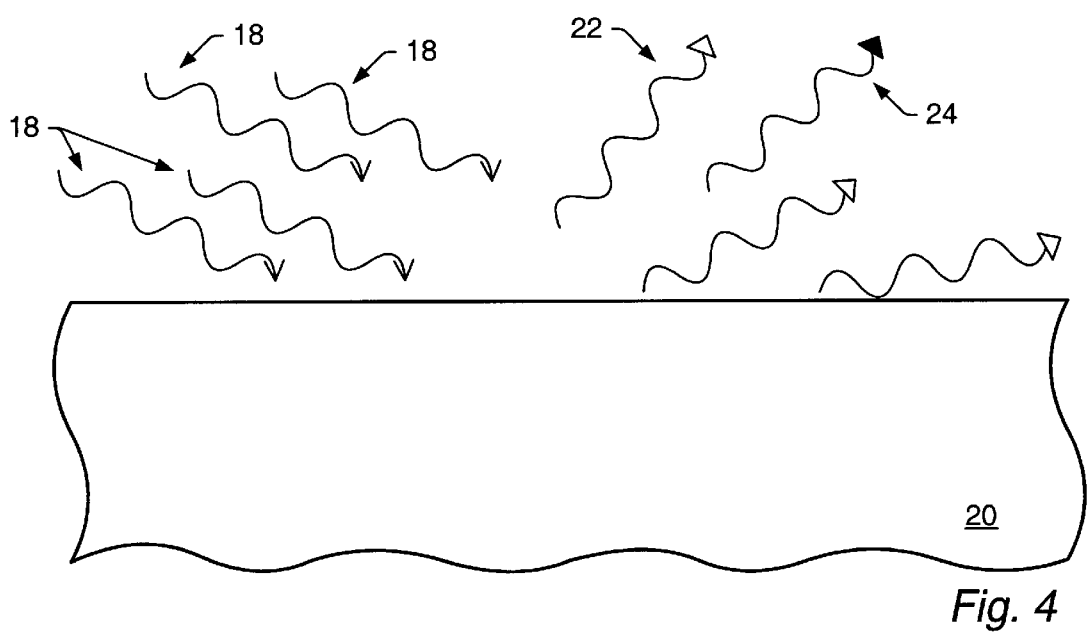
*Fig. 4*
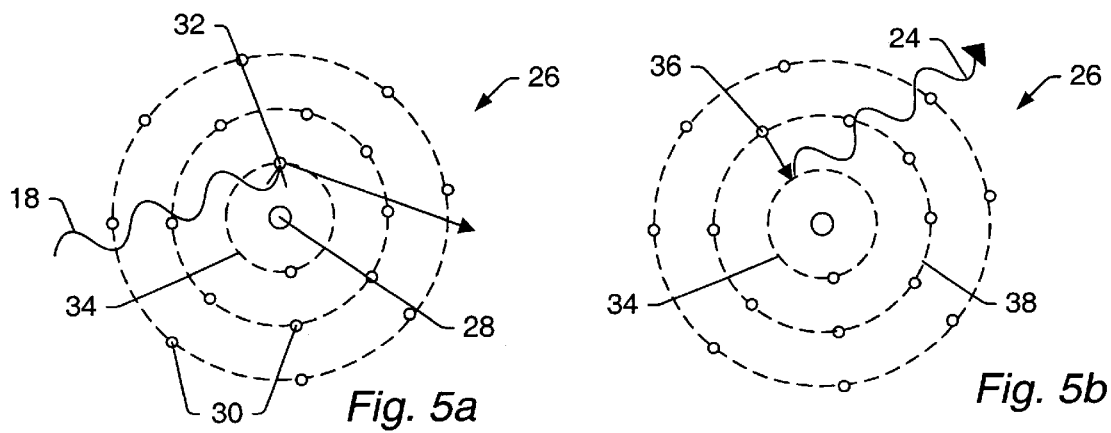
*Fig. 5a*
*Fig. 5b*

SCATTERED INCIDENT X-RAY PHOTONS FOR MEASURING SURFACE ROUGHNESS OF A SEMICONDUCTOR TOPOGRAPHY

BACKGROUND OF THE INVENTION

1 Field of the Invention

This invention relates to integrated circuit manufacturing and more particularly to determining the roughness of an unpatterned surface of a semiconductor topography.

2. Description of the Relevant Art

Fabrication of an integrated circuit is a complex process involving numerous steps. To form a metal-oxide-semiconductor (MOS) transistor, for example, a gate dielectric is formed on a semiconductor substrate which is doped with either n-type or p-type impurities. A gate conductor is formed over the gate dielectric, and dopant impurities are introduced into the substrate to form a source and drain. Such transistors are connected to each other and to terminals of the completed integrated circuit using conductive interconnect lines.

A pervasive trend in modern integrated circuit manufacture is to produce transistors having feature sizes as small as possible. Many modern day processes employ features, such as gate conductors and interconnects, which have less than 1.0 $\mu$m critical dimension. As feature size decreases, the sizes of the resulting transistors as well as that of the interconnects between transistors also decrease. Fabrication of smaller transistors allows more transistors to be placed on a single monolithic substrate, thereby allowing relatively large circuit systems to be incorporated on a single, relatively small die area.

This trend toward reduced feature sizes imposes severe demands on the lithography processes used to define features in integrated circuit fabrication. In a lithography process, a film of a radiation-sensitive material called photoresist is typically formed upon the surface of the material to be patterned. This photoresist film is then exposed through a mask to radiation. Portions of the photoresist which are exposed to the radiation undergo a chemical change, such that subsequent use of a chemical called a developer will exclusively remove either the exposed or unexposed resist portions. In this way, the mask pattern may be transferred to the photoresist. The retained photoresist may then be used as a mask for subsequent etching or doping of the underlying material, thereby transferring the mask pattern to this material. Complications with photolithography processes can occur, however, which cause the feature sizes of the patterned material to be different than those of the mask. Such feature size differences become even more significant as feature size is reduced, and the "error" in the patterned dimension may approach the magnitude of the intended dimension itself.

One source of feature size error in photolithography processes may be scattering of exposing radiation from rough surfaces underlying a photoresist film. A situation in which this may occur is illustrated in FIG. 1. Photoresist film 2 is formed over material 4 which has a rough upper surface. Exposing radiation 6 is directed into photoresist film 2 through a transparent portion of mask 8. An enlarged view including the interface between photoresist film 2 and underlying material 4 is shown in FIG. 2. In FIG. 2, incident exposing radiation photons 10 are represented using open arrowheads. Some of incident photons 10 not absorbed by photoresist film 2 or transmitted to underlying material 4 may be scattered at upper surface 14 of material 4, producing scattered photons 12, indicated using filled arrowheads.

It is postulated that increased roughness of surface 14 increases the variation in scattering angles exhibited by scattered photons 12. A large variation in scattering angles is in turn believed to increase the likelihood that scattered photons 12 may penetrate portions of photoresist layer 2 external to the portion subtended by mask feature width $W_m$. The boundaries of this intended feature width are shown by dashed lines in FIG. 2.

This scattering of exposing radiation into portions of photoresist film 2 external to the intended feature width results in an increased exposed portion of photoresist film 2, as shown in FIG. 3. Exposed portion 16 of photoresist film 2 extends beyond the boundaries of intended feature width $W_m$, so that the width $W_p$ of the feature transferred to the photoresist is larger than $W_m$. An error of $W_p$-$W_m$ is therefore incurred in the transfer of the mask feature to the photoresist. This error may be particularly significant for small intended feature width $W_m$, since $W_p$-$W_m$ may become comparable to $W_m$. For very small intended feature sizes of approximately 0.25 micron or less, root-mean-square (RMS) roughness values on the order of tens of angstroms or less are believed to be capable of producing significant error. Monitoring of roughness values for surfaces of layers to be patterned may therefore be extremely important.

Atomic force microscopy (AFM) is a currently-used technique for determining surface roughness. AFM involves high-resolution scanning (angstrom resolution) of a probe held extremely close to a surface. The chemical force between the probe tip and surface is measured during the scan, producing a high-resolution scan of the surface topography from which RMS roughness may be obtained. AFM can produce accurate measurements of RMS roughness values as low as about 0.5 angstroms, but this accuracy comes at a high cost in measurement time. An AFM scan of an area a few microns on a side may require tens of minutes, or even longer, to perform. To obtain a roughness value characteristic of the overall surface of a semiconductor topography, which is typically formed upon a substrate having a diameter of 8 inches or more, would require sampling multiple areas and could take many hours to obtain by AFM.

In addition to the long measurement times needed for AFM measurement of roughness, sample damage using AFM is also a possibility. Although AFM is theoretically non-destructive, the very close proximity of the measurement tip to the sample allows the possibility of "tip crashes", in which the tip comes into forceful contact with the sample surface during a measurement. Such contact can cause scraping and/or scratching of the surface. In one mode of AFM operation, known as contact mode, the probe tip is in constant contact with the sample surface, which may cause sample damage.

It would therefore be desirable to develop a method for relatively rapid and non-destructive determination of roughness on surfaces of materials used in semiconductor manufacturing. The method should allow determination of roughness over larger areas of a surface than are conveniently scanned using AFM.

SUMMARY OF THE INVENTION

The problems outlined above are addressed by a method using a glancing-angle X-ray fluorescence (XRF) technique in combination with calibration standards to determine the roughness of a target surface. In conventional XRF techniques, a beam of primary X-rays is directed at the surface of a semiconductor wafer, and the energies (or corresponding wavelengths) of resultant secondary X-rays emitted by atoms of elements on and just under the surface of the wafer are measured. Atoms of elements in target materials emit secondary X-rays with uniquely characteristic energies. Thus the elemental compositions of materials on and just under the surface of the wafer may be determined from the measured energies of emitted secondary X-rays. In the glancing-angle XRF technique recited herein, a signal containing primary X-rays scattered from the sample surface is analyzed, in addition to a secondary X-ray beam. A plot of the emitted secondary beam strength versus scattered primary beam strength exhibits a characteristic slope. This slope corresponds to a particular value of RMS roughness, which may be determined using a direct imaging or profiling technique such as AFM. After a calibration curve or table relating slope to RMS roughness is generated, subsequent roughness measurements may be performed using only XRF and comparison to the calibration data, without a requirement for further time-consuming AFM measurements.

The glancing-angle XRF measurement may be made using an XRF spectrometer capable of glancing-angle scattering geometries. Such a spectrometer may be obtained commercially. The XRF spectrometer produces a monochromatic primary X-ray beam, which is typically incident upon the sample surface at an angle between about 0.01° and about 0.1°, relative to that surface. Upon interaction with the sample surface, this incident primary beam may be converted into beams which include a scattered primary beam and one or more emitted secondary fluorescence beams. A variation in scattered primary and emitted secondary beam intensities may be produced by altering the experimental configuration, preferably by changing the angle of incidence of the incident beam. Other methods, such as changing the power of the incident beam, may also be suitable for achieving this variation. This variation of the beam intensities allows a set of intensity values to be generated which can subsequently be used to plot secondary beam intensity vs. scattered primary beam intensity. The spectrometer includes an X-ray detector which collects portions of the scattered primary and emitted secondary radiation. The detector is preferably configured directly above the illuminated portion of the surface, in what is known as a total XRF (TXRF) geometry. For each experimental configuration, the output of the detector and associated electronics is typically a plot of intensity versus energy of the collected radiation. The intensities of the scattered primary beam and an emitted secondary beam are recorded for each experimental configuration, typically using a computer associated with the XRF spectrometer.

After collecting data for a series of experimental configurations, intensity of the emitted secondary beam is plotted versus that of the scattered primary beam, and the slope of the plot determined. This slope may be compared to calibration data correlating slope to RMS roughness measured by, for example, AFM. In this manner, RMS roughness of the surface may be determined using a glancing-angle XRF technique. Calibration data may be obtained for each material surface to be studied. It is believed that this is not necessary, however, because the relationship between roughness and slope using the method recited herein has been found to be substantially identical for a range of material surfaces, including silicon, aluminum, titanium, titanium nitride, and silicon dioxide. It is contemplated that this method can measure RMS roughness values which vary in a range from about 1 to about 100 angstroms in topographical elevational disparity. This range of roughness values is relevant to many situations which arise in semiconductor fabrication. For example, an as-deposited polysilicon surface typically exhibits RMS roughness of about 50 angstroms. It is contemplated that this roughness may be reduced using a technique such as chemical-mechanical polishing (CMP). The method recited herein is therefore believed to be useful in monitoring both as-deposited and as-polished polysilicon surfaces. As another example, a tungsten surface which has been planarized by CMP (during, for example, an interconnect formation process) typically exhibits RMS roughness of about 50 angstroms.

In the glancing-angle XRF method recited herein, no mechanical contact is made to the top surface of the sample, so that no surface damage results. No sample preparation is required, and the method is not destructive to the sample. The area on the sample surface from which scattered and/or emitted radiation is detected is typically approximately 2 cm in diameter. Measurement from one such area of the sample, including sample positioning and variation of experimental conditions for data collection, is estimated to require approximately 15 minutes. The measurement area of the method recited herein is therefore believed to be greater, and the measurement time shorter, than those typically achievable using other techniques such as AFM. This increased measurement area and rapidity of measurement may provide greatly increased convenience and throughput for semiconductor process monitoring.

BRIEF DESCRIPTION OF THE DRAWINGS

Other objects and advantages of the invention will become apparent upon reading the following detailed description and upon reference to the accompanying drawings in which:

FIG. 3 is a partial cross-sectional view of the topography of FIG. 1 illustrating an exposed portion of the photoresist film, subsequent to the exposure of FIG. 1;

FIG. 4 is a partial cross-sectional view of primary X-ray photons incident upon a target material and scattered primary photons and an emitted secondary photon leaving the target material;

FIG. 5a is a representation of an atom of the target material of FIG. 4, wherein a primary X-ray photon is incident upon the atom, and wherein the entire energy of the primary X-ray photon is absorbed by the atom, resulting in the ejection of an electron in a "K" shell from the atom;

FIG. 5b is a representation of the atom of FIG. 5a following ejection of the K-shell electron, wherein an electron in an "L" shell of the atom fills the vacancy in the K shell, and wherein the atom simultaneously emits a secondary X-ray photon;

Figure 1:
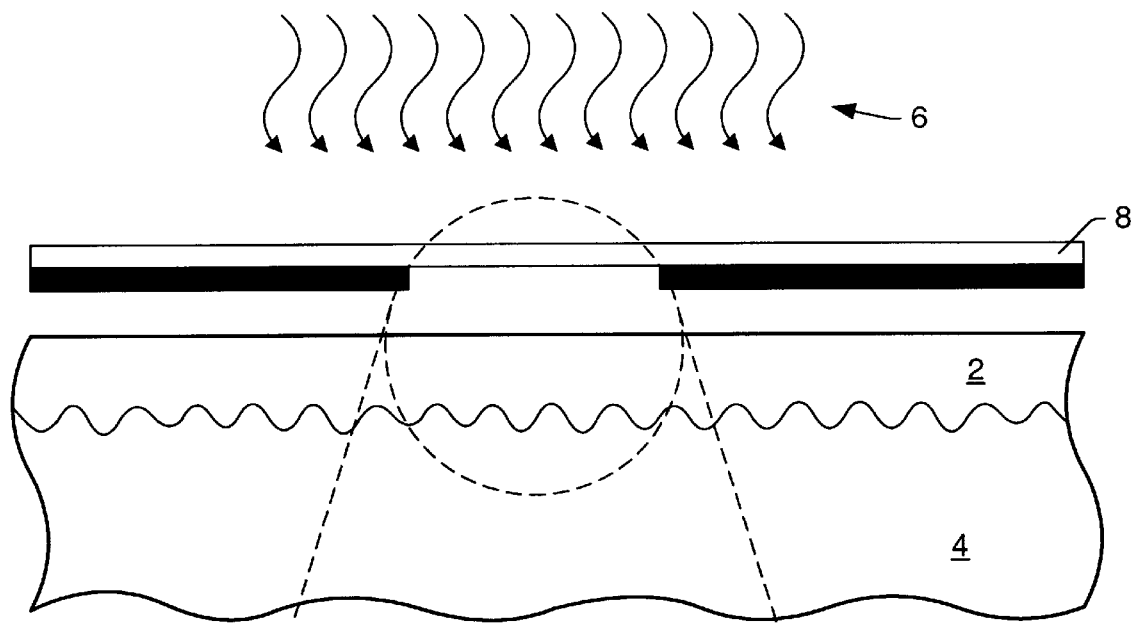
FIG. 1 is a partial cross-sectional view of the exposure through a mask of a semiconductor topography including a photoresist film formed upon a material to be patterned.
Figure 2:
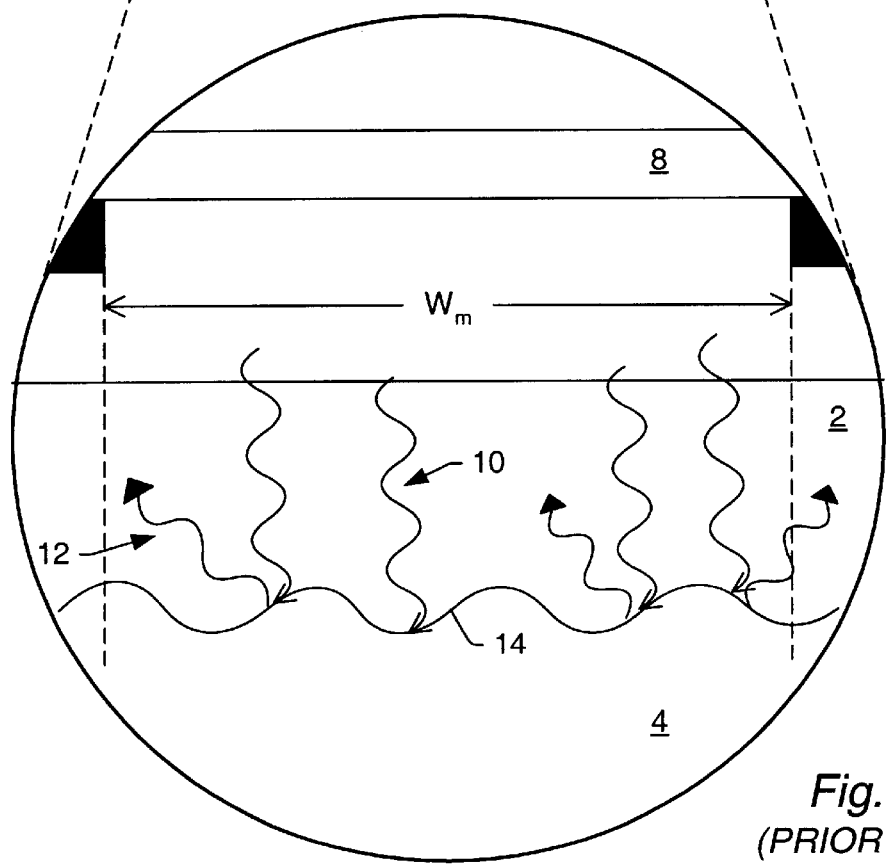
FIG. 2 is an expanded view of the interface between the photoresist film and underlying material of FIG. 1.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, FIG. 4 is a partial cross-sectional view representing an XRF experiment. Primary X-ray photons 18 are incident upon the upper surface of target material 20. Primary photons 18 are preferably monochromatic (having the same frequency). Although it may be possible to measure roughness using the method recited herein with a polychromatic incident beam, comparing intensities of scattered and secondary peaks is believed to be more difficult in this case. Target material 20 is preferably an unpatterned material at the surface of a semiconductor topography. Examples of suitable materials may include an unpatterned silicon wafer, a dielectric layer formed over a silicon wafer, a deposited polysilicon layer before patterning to form transistor gates, and a deposited metal layer before patterning to form interconnects. Interaction of incident photons 18 with material 20 may result in elastically scattered primary photons, such as photons 22 (indicated with open triangular arrowheads in FIG. 4), having the same frequency as incident photons 18. Secondary X-ray photons such as photon 24 (indicated with a filled triangular arrowhead) may also be emitted.

The process by which secondary X-ray photons are emitted is illustrated in FIGS. 5a and 5b. FIG. 5a is a representation of an atom 26 of target material 20. In the simple atomic model shown, atom 26 has a nucleus 28 surrounded by electrons 30 at different discrete energies from nucleus 28 called electron shells. The electron shells may also be interpreted as orbits at discrete distances from the nucleus within which the shell electrons move. A given electron shell has an associated binding energy equal to the amount of energy required to remove an electron from the electron shell. The binding energy of an electron shell is inversely related to the energy difference between the electron shell and the nucleus, and to the distance of the shell from the nucleus. The innermost electron shell of an atom is called the K shell, and has the highest binding energy level associated with it. In FIG. 5a, K-shell electron 32 is located in K shell 34.

FIG. 5a also shows primary X-ray photon 18 impacting atom 26 within target material 20. If the energy E of primary X-ray photon 18 is greater than the binding energy $\phi_K$ associated with K shell 34, the entire energy of primary X-ray photon 18 may be absorbed by atom 26, and one of the electrons in K shell 34 may be ejected from atom 26. As depicted in FIG. 5a, K-shell electron 32 is ejected from atom 26 after primary X-ray photon 18 is absorbed by atom 26. K-shell electron 32 is ejected with a kinetic energy of $(E-\phi_K)$.

With a vacancy in K shell 34, atom 26 is energetic and unstable. The most probable stabilization mechanism is the filling of the vacancy in K shell 34 by an electron located in an electron shell with a lower binding energy level. As shown in FIG. 5b, an L-shell electron 36 in L shell 38, farther from nucleus 28 than K shell 34, may fill the vacancy in K shell 34. As L-shell electron 36 fills the vacancy in K shell 34, atom 26 simultaneously emits secondary X-ray photon 24 with energy $(\phi_K-\phi_L)$, where $\phi_L$ is the binding energy level of L shell 38. With a vacancy now in L shell 38, ionized atom 26 is more stable and less energetic. The energy levels (or corresponding wavelengths) of secondary X-ray photons emitted by atoms of elements in substances on and just under the surface of a target material are uniquely characteristic, allowing the elemental compositions of the substances to be determined.

Figure 6:
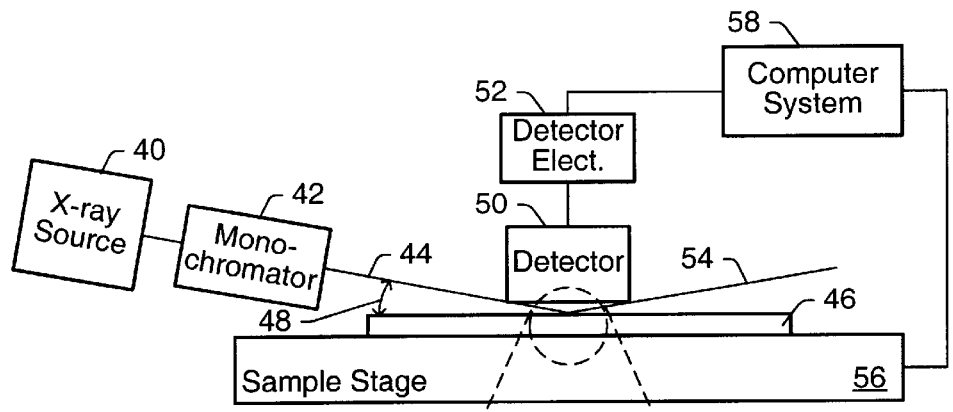
FIG. 6 is a side elevation view of portions of a total X-ray fluorescence (TXRF) spectroscopy apparatus suitable for the method recited herein.

A side elevation view illustrating key aspects of an apparatus which may be used in the method recited herein is shown in FIG. 6. X-ray source 40 and monochromator 42 provide monochromatic incident X-ray beam 44, which is incident upon the upper surface of sample 46 at angle 48. X-ray source 40 is typically an X-ray tube, in which accelerated electrons excite X-ray emission from a metal anode material. This excitation process is similar to that shown in FIGS. 5a and 5b, with incident X-ray photon 18 replaced by an electron. The anode metal in the X-ray tube is chosen to ensure that the emitted X-rays have sufficient energy to excite fluorescence in the material being studied. In general, higher-energy X-ray transitions occur in higher-atomic-number atoms. X-ray tube anode materials are therefore typically metals with relatively high atomic number. Examples of anode materials include gold, chromium, molybdenum and tungsten. Alternatively, X-ray source 40 may be a different type of source, such as a radioisotope source or a rotating anode generator.

For sources which emit X-rays at more than one frequency, monochromator 42 of FIG. 6 may be used to form a monocrystalline incident beam. Monochromator 42 typically includes a dispersive element, and may include a collimating element. Suitable dispersive elements may include single crystals or multilayer mirror structures. The parallel planes inherent to crystals and multilayer structures serve to selectively reflect specific wavelengths through Bragg reflection. Collimating elements typically include closely-spaced metal plates or tubes which absorb all but parallel photons. Monochromator 42 may include a filtering element, in addition to or instead of the dispersive element described above. If X-ray source 40 produces a sufficiently monochromatic beam (as may be the case, for example, with many radioisotope sources), monochromator 42 may be omitted.

Angle 48, at which monochromatic X-ray beam 44 is incident upon sample 46, is preferably between about 0.01° and about 0.1°. This glancing angle helps to prevent a large portion of the elastically scattered radiation from reaching the detector, which keeps the scattered photon signal from overwhelming the secondary X-rays emitted from the sample. In this way, identification of sample atoms is facilitated, while sufficient scattered photons are collected to allow the plotting of secondary vs. scattered photons recited herein. Sample 46 is preferably a semiconductor wafer having a material similar to target material 20 of FIG. 4 at its surface. Surface roughness of other types of sample may also be determined by this method, however. The sample must only be of a size and shape which allow it to be mounted in an XRF apparatus similar to that of FIG. 6. The material at the surface of sample 46 is preferably of greater thickness than the escape depth of the incident X-rays in the material. In this way, the secondary X-ray photons detected are from only the uppermost material layer of the sample, which may simplify the plotting of secondary vs. scattered X-ray intensity. A suitable thickness of the uppermost material layer may be greater than or equal to about 300 angstroms.

X-ray detector 50 and detector electronics 52, also shown in FIG. 6, are used to measure the intensity of the X-ray photons which reach the detector as a function of energy. Detector 50 is positioned facing and directly above the portion of the surface of sample 46 which is illuminated by incident primary X-ray beam 44, and is typically very close to the surface of sample 46. The spacing between detector 50 and sample 46 is preferably less than 1 centimeter, and typically approximately 2 millimeters. Detector 50 is typically a semiconductor diode which produces an electrical output signal proportional to the energy of in incident X-ray photon. Lithium-drifted silicon detectors and high-purity Ge detectors are examples of such semiconductor diode detectors. Alternatively, other types of detector may be used, such as scintillation detectors which produce an optical output signal proportional to the energy of an incident X-ray photon. This optical output signal is converted to electrical pulses using, for example, a photomultiplier tube. Thallium-doped sodium iodide is a typical scintillation detector material. The output signal from X-ray detector 50 is typically processed by detector electronics 52 to provide data showing the intensity of X-ray radiation collected as a function of energy. Detector electronics 52 may include energy-sorting electronics, such as a multi-channel analyzer, and amplification electronics. Some or all of detector electronics 52 may be combined in the same package as detector 50. Scattered primary beam 54 contains X-ray photons reflected from the surface of sample 46 at an angle of 180° minus incident angle 48. Scattered beam 54 is therefore not collected by detector 50. A small fraction of the total primary photons scattered are scattered at larger angles than that of beam 54, particularly when the surface of sample 46 is rough. Such scattered photons may be collected by detector 50, and are discussed in more detail with reference to FIG. 7 below.

In the embodiment of FIG. 6, sample 46 is mounted upon sample stage 56. Sample stage 56 is designed to move in order to facilitate sample loading and alignment of selected areas of sample 46 with incident beam 44 for analysis. Movement of sample stage 56 and collection of data using detector 50 and detector electronics 52 are typically automated using a computer system such as computer system 58 in FIG. 6. Additional motion control electronics may also be used in movement of sample stage 56. Other parts of a typical XRF system not shown in FIG. 6 may include an enclosure to shield the sample and detector from stray light, and a vacuum chamber surrounding the sample and vacuum pump which may be used to prevent absorption of X-rays by the ambient.

Figure 7:
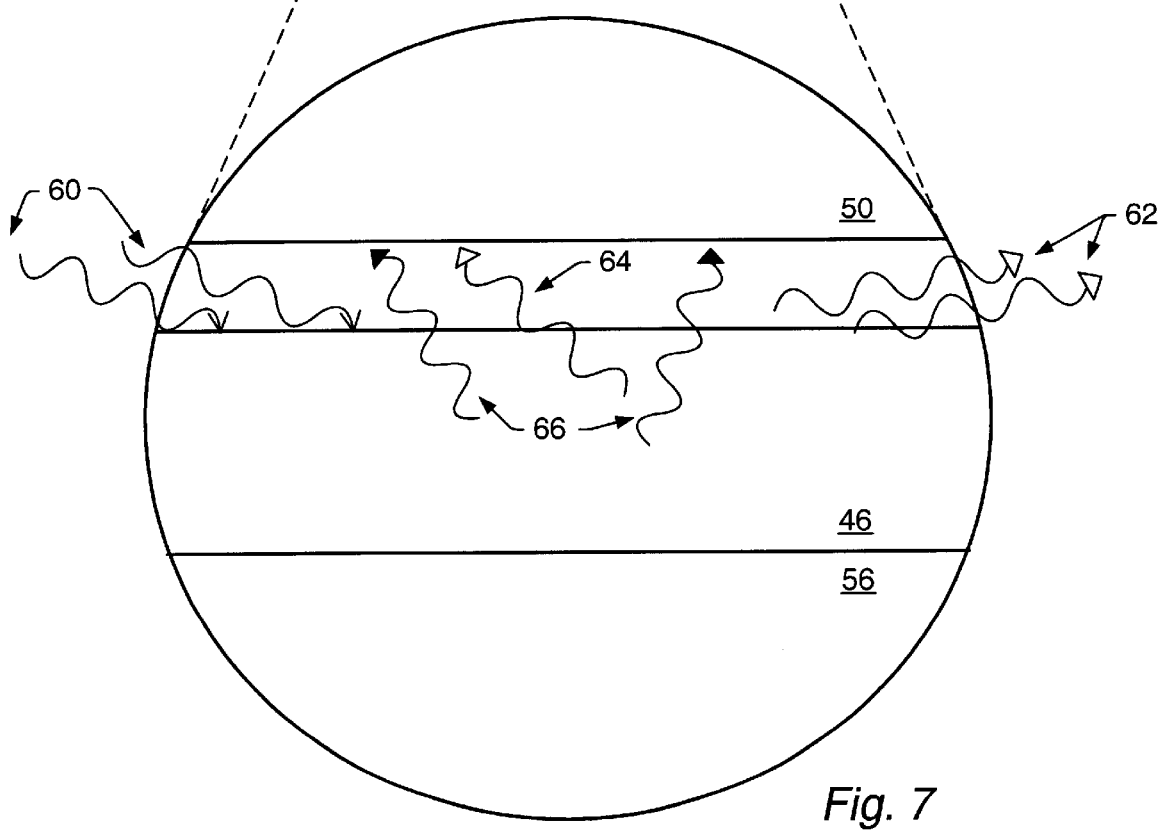
FIG. 7 is an expanded view including the sample surface in the vicinity of the X-ray detector of the apparatus of FIG. 6.

The circular portion bounded by a dashed line in FIG. 6 is shown in an expanded view in FIG. 7. Incident primary photons 60 form a part of incident beam 44 of FIG. 6. Upon interaction with sample 46, some of photons 60 may become elastically scattered photons, such as photons 62 and 64 of FIG. 7 (indicated with open triangular arrowheads). Photons 62 form a part of reflected beam 54 shown in FIG. 6. A small fraction of the elastically scattered photons, such as photon 64 in FIG. 7, are scattered in different directions than that of reflected beam 54. Some of photons 64 may be collected by detector 50. Some of photons 60 may excite secondary photons 66, indicated with filled triangular arrowheads in FIG. 7. Secondary photons 66 are emitted in all directions, and some of photons 66 may be collected by detector 50.

The XRF geometry of FIGS. 6 and 7, in which a glancing incidence angle is used and the detector is oriented at normal incidence to the substrate surface, is also known as a TXRF geometry. The TXRF configuration, by keeping a large fraction of the elastically scattered photons out of the detector, prevents the scattered signal from "swamping" the secondary photon signal. The intensities of the scattered and secondary X-ray signals detected in a TXRF apparatus are typically of comparable magnitude. This is convenient for the plotting of secondary vs. scattered radiation which is performed as a part of the method recited herein.

Figure 8:
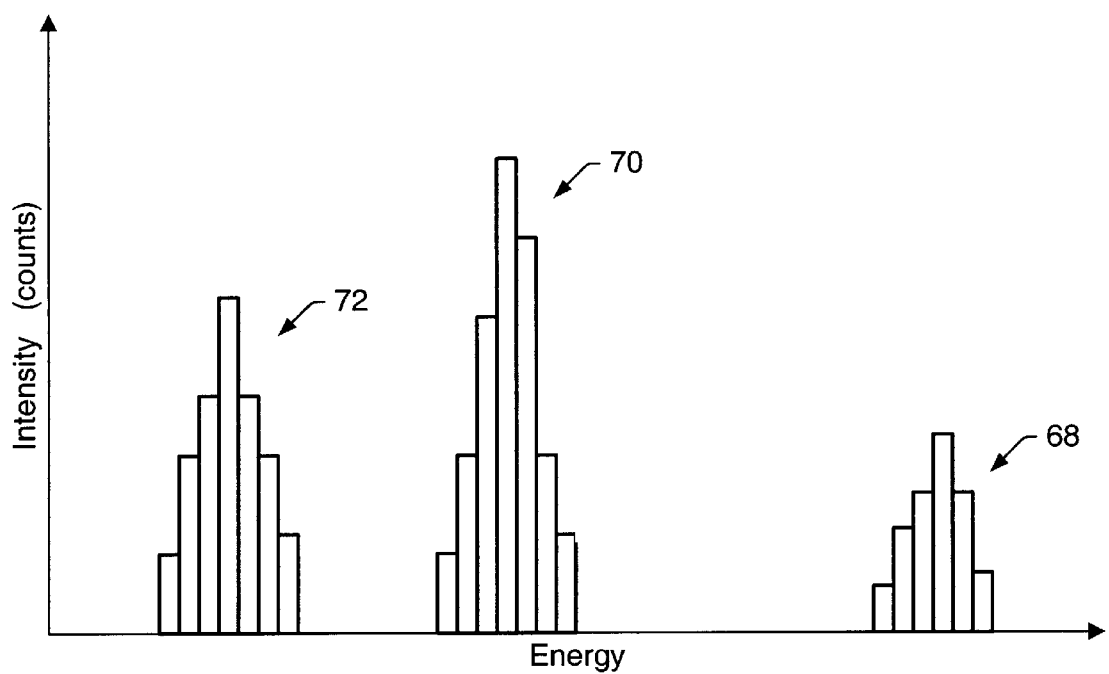
FIG. 8 is a representative graph of counts vs. energy of photons collected by the detector of the apparatus of FIG. 6.

A representative graph of X-ray intensity, in units of number of X-rays counted during a particular collection time, vs. energy is shown in FIG. 8. Such a graph may be generated, for example, by computer system 58 of FIG. 6, using data from detector 50 and detector electronics 52. The graph is in the form of a histogram, in which the energy range plotted has been divided into several energy subranges, and the number of X-ray photons detected having an energy within each subrange is plotted. Such sorting of detected photons into energy subranges is often performed using a multi-channel analyzer. Other methods of obtaining an X-ray intensity vs. energy plot may also be suitable, however. For example, a monochromator could be used between the sample and detector and scanned to produce a continuous plot of intensity vs. energy. Such an arrangement could necessitate using a different scattering geometry than the TXRF geometry of FIG. 6, however, which could change the relative peak intensities. In the representative graph of FIG. 8, highest-energy peak 68 represents the detected scattered primary radiation. Peaks 70 and 72 represent secondary X-ray peaks. Because the surface layer of the sample may be a compound, such as $SiO_2$, rather than a single-element material, and each element present has a unique XRF signature, multiple secondary peaks are possible.

Figure 9:
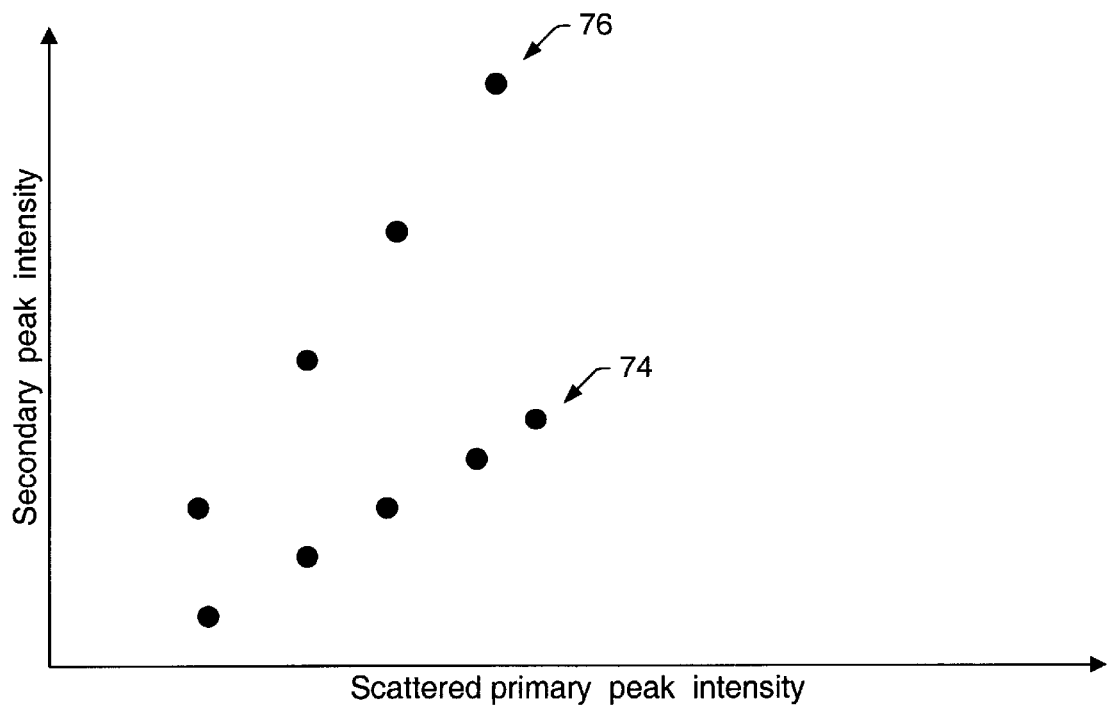
FIG. 9 is a representative graph of emitted secondary X-ray intensity versus scattered primary X-ray intensity for surfaces having two different RMS roughness values.

Any of these secondary peaks may be used to form a plot of secondary peak intensity vs. scattered primary peak intensity, as shown in FIG. 9. To form the plot of FIG. 9, a series of intensity vs. energy plots such as that of FIG. 8 are typically recorded, using a series of slightly altered experimental conditions. The experimental conditions are preferably altered by changing the angle of incidence of the primary beam within a range of about 0.01° to about 0.1°. Other methods of changing the experimental conditions may also be suitable, such as changing the power of the incident beam. From each of the series of intensity vs. energy plots, the intensity of a secondary peak and the intensity of the scattered primary peak are plotted as coordinates of a point on the secondary vs. primary intensity graph of FIG. 9. The same secondary peak is used throughout when plotting secondary intensity vs. scattered primary intensity points for a given sample. Plotting the sum of multiple secondary peak intensities from a graph such as that of FIG. 8, rather than choosing a single secondary peak, may also provide similar results. The intensities plotted are preferably integrated intensities, i.e. the area under a peak such as peak 68 in FIG. 8. Alternatively, peak intensity values may also be suitable.

The points plotted for a given sample are believed to form a line. In FIG. 9, set of points 74 is plotted using intensity vs. energy data for one sample, while set of points 76 is plotted for a different sample. The slope of the line formed by the points plotted on the graph of FIG. 9 is believed to be related to the roughness of the upper surface of the corresponding sample. In the embodiment of FIG. 9, for which secondary peak intensity is plotted on the vertical axis, the slope is believed to be greater for samples having rougher surfaces. Therefore, the sample corresponding to set of points 76 is believed to have a rougher upper surface than the sample corresponding to set of points 74. Alternatively, a plot similar to that of FIG. 9 could be made with the scattered primary peak intensity on the vertical axis. In such an embodiment, the slope is believed to be greater for samples having smoother surfaces.

The mechanisms responsible for the dependence of the slopes of the lines shown in FIG. 9 on the roughness of the corresponding samples are not completely known. It may be postulated that experimental conditions which cause an increased collection of scattered primary photons by the detector, such as an increased angle of incidence of the primary beam, also cause an increased emission of secondary photons which are captured by the detector. The strength of this enhancement of secondary photon yield when more scattered primary photons reach the detector corresponds to the slope of the secondary vs. scattered primary intensity plot. This slope is observed to be higher for rougher sample surfaces, as noted above. It is observed that higher angles of incidence (within the range of small incidence angles used in a TXRF geometry) produce higher yields of scattered primary X-rays in the detector, as well as higher yields of emitted secondary X-rays. It is postulated that the irregular surface orientation of a rough surface presents presents a locally larger angle of incidence to a fraction of the incident primary photons, resulting in an increase in both scattered primary X-rays and emitted secondary X-rays reaching the detector. On average, the greater the RMS roughness value, the greater the increase in effective angle of incidence is believed to be.

To find the actual roughness corresponding to a set of secondary vs. scattered primary intensity points such as sets 74 and 76 of FIG. 9, the slope of the line formed by the set of points is determined. The slope is then compared to calibration data to determine the actual roughness. The calibration data is generated by measuring both the secondary vs. scattered intensity slope described above and the actual roughness using a direct imaging or profiling technique on a series of samples with varying roughness. Such calibration data may be arranged in various forms, including tables or plotted curves. The direct roughness measurement is preferably performed by AFM, but other techniques, such as scanning tunneling microscopy or transmission electron microscopy, may also be suitable. Calibration data may be generated for each sample material to be studied, but this is believed to be unnecessary, as noted above. Slope vs. roughness relationships have been found to be identical for a range of sample materials, including silicon, silicon dioxide, titanium, aluminum, and titanium nitride.

Figure 10:
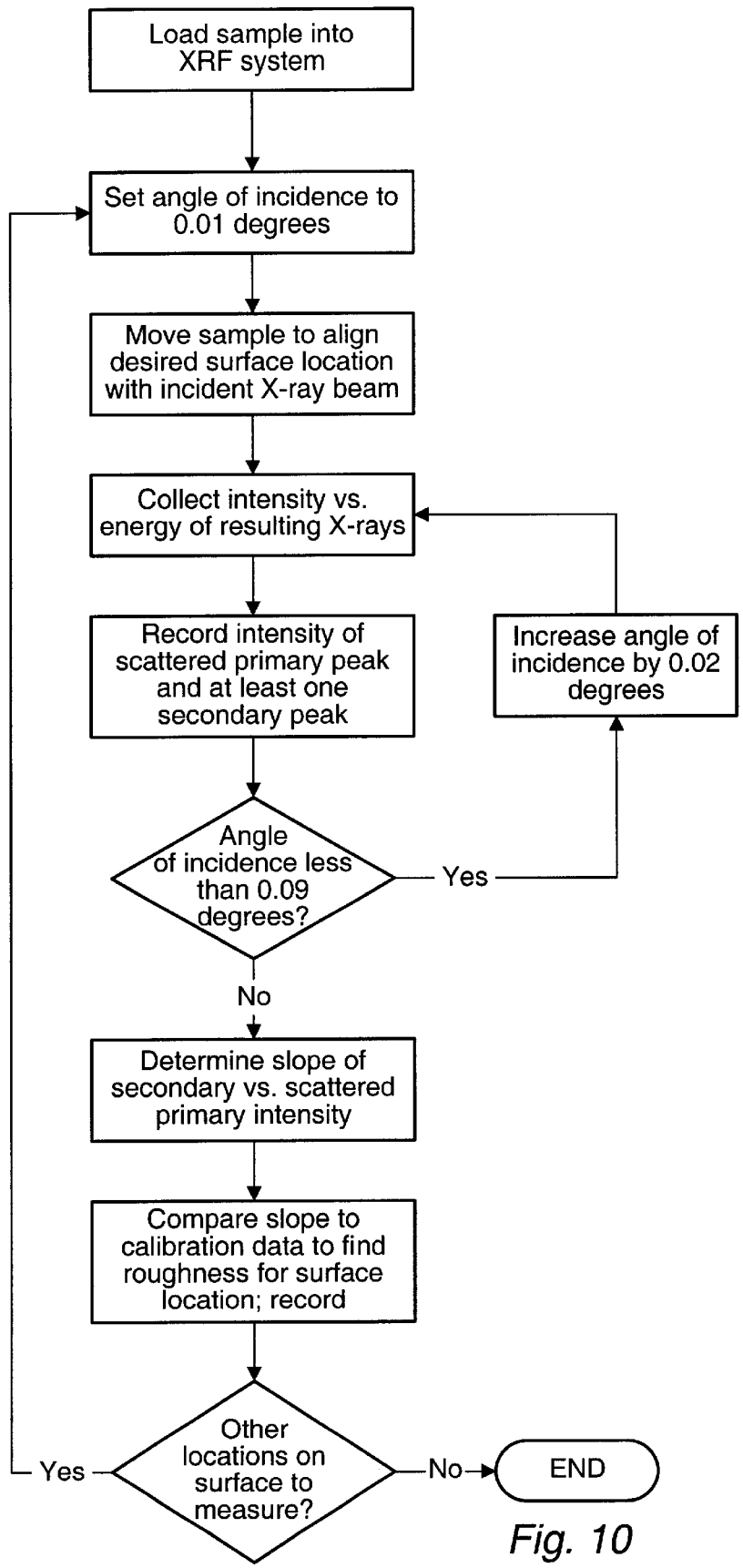
FIG. 10 is a flow diagram illustrating an embodiment of the method recited herein.

Turning now to FIG. 10, a flow diagram illustrating an embodiment of the method is shown. A sample is first loaded into an XRF system, such as the system illustrated in FIG. 6. In the embodiment of FIG. 10, the angle of incidence of the incident primary X-ray beam is set to 0.01 degrees. A different starting angle may also be used. The sample is moved, preferably using a movable sample stage such as stage 56 in FIG. 6, to align the desired measurement location on the sample surface with the area illuminated by the incident X-ray beam. The intensities of scattered primary and emitted secondary X-rays are then measured as a function of energy, preferably using a detector such as detector 50 and detector electronics such as electronics 52 shown in FIG. 6. A plot of these intensities vs. energy contains a peak corresponding to scattered primary X-rays, and at least one secondary X-ray peak. The intensities of the scattered primary peak and at least one of the secondary peaks is recorded. The intensities may be recorded in various formats, such as integrated intensity or peak intensity, as discussed above. The angle of incidence is then incremented so that intensity measurements may be obtained using a different angle of incidence. In the embodiment of FIG. 10, the angle is incremented by 0.02 degrees, so that measurements are made at 0.01°, 0.03°, 0.05°, 0.07°, and 0.09°.

The slope of a plot of secondary peak intensity vs. scattered primary peak intensity for the above measurements is then determined. This slope is compared to calibration data in order to determine the roughness at the surface location measured, completing the roughness measurement for this location. The process may be repeated if measurement at additional locations on the sample surface is desired. Performance of some or all of the operations included in the flow diagram of FIG. 10 may be assisted or controlled by a computer, such as computer system 58 of FIG. 6. In other embodiments, it may be possible to obtain a suitable set of points for slope determination by varying a different parameter than angle of incidence. For example, variation of incident X-ray power may also be suitable.

It will be appreciated by those skilled in the art having the benefit of this disclosure that this invention is believed to provide a method for measuring the roughness of a surface of a target material based upon comparing intensities of scattered incident X-ray photons with those of emitted secondary photons. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. A method for determining a roughness value of a surface, comprising:

exposing the surface to a primary X-ray beam;

collecting a secondary X-ray peak and a scattered primary X-ray peak using an X-ray detector;

recording a secondary peak intensity and a scattered primary peak intensity for each of a series of experimental configurations to form a set of secondary peak intensity values and a set of scattered primary peak intensity values;

plotting the set of secondary peak intensity values versus the set of scattered primary peak intensity values to determine a slope; and comparing the slope to calibration data to determine the roughness value of the surface.

2. The method as recited in claim 1, wherein said exposing comprises illuminating an unpatterned surface of a semiconductor topography with a monochromatic X-ray beam.

3. The method as recited in claim 2, wherein said illuminating an unpatterned surface comprises illuminating a silicon surface.

4. The method as recited in claim 2, wherein said illuminating an unpatterned surface comprises illuminating an oxide surface.

5. The method as recited in claim 2, wherein said illuminating an unpatterned surface comprises illuminating a surface of a material selected from the group consisting of titanium, tungsten, aluminum, and titanium nitride.

6. The method as recited in claim 1, wherein said exposing comprises using an incident angle between the primary X-ray beam and the surface of less than about 0.2 degrees.

7. The method as recited in claim 6, wherein said exposing further comprises using an incident angle between about 0.01 degrees and about 0.1 degrees.

8. The method as recited in claim 1, wherein said exposing comprises using an X-ray source voltage between about 20 kV and about 30 kV.

9. The method as recited in claim 7, wherein said exposing comprises using an X-ray source current between about 50 mA and about 400 mA.

10. The method as recited in claim 1, wherein said exposing comprises using an X-ray tube source.

11. The method as recited in claim 9, wherein said using an X-ray tube source comprises using a tube comprising gold.

12. The method as recited in claim 9, wherein said using an X-ray tube source comprises using a tube comprising tungsten, molybdenum, or chromium.

13. The method as recited in claim 1, wherein said collecting further comprises positioning a detector directly above and facing an area of the surface illuminated by the primary X-ray beam.

14. The method as recited in claim 13, wherein said positioning a detector further comprises using a spacing between the detector and the surface of less than or equal to about 1 centimeter.

15. The method as recited in claim 1, wherein said collecting comprises using a high-purity germanium detector.

16. The method as recited in claim 1, wherein said collecting comprises using a scintillation detector.

17. The method as recited in claim 1, wherein said collecting further comprises determining a relative number of X-ray photons received by the X-ray detector within a predetermined collection time, as a function of X-ray photon energy.

18. The method as recited in claim 1, wherein said recording further comprises recording an integrated intensity of the secondary X-ray peak and an integrated intensity of the scattered primary X-ray peak.

19. The method as recited in claim 1, wherein said comparing comprises comparing to data including atomic force microscopy measurement results.

* * * * *